US010368609B2

(12) United States Patent
Ma et al.

(10) Patent No.: US 10,368,609 B2
(45) Date of Patent: Aug. 6, 2019

(54) MASSAGING SHOE AND METHOD FOR MANUFACTURING THE SAME

(71) Applicant: SHENZHEN BREO TECHNOLOGY CO., LTD., Shenzhen (CN)

(72) Inventors: Xuejun Ma, Shenzhen (CN); Daming Yu, Shenzhen (CN); Huchen Zhao, Shenzhen (CN)

(73) Assignee: SHENZHEN BREO TECHNOLOGY CO., LTD., Shenzhen (CN)

( * ) Notice: Subject to any disclaimer, the term of this patent is extended or adjusted under 35 U.S.C. 154(b) by 16 days.

(21) Appl. No.: 15/121,677

(22) PCT Filed: Jun. 20, 2016

(86) PCT No.: PCT/CN2016/086475
§ 371 (c)(1),
(2) Date: Aug. 25, 2016

(87) PCT Pub. No.: WO2017/054527
PCT Pub. Date: Apr. 6, 2017

(65) Prior Publication Data
US 2017/0265563 A1 Sep. 21, 2017

(30) Foreign Application Priority Data
Dec. 31, 2015 (CN) .......................... 2015 1 1031242

(51) Int. Cl.
*A61F 5/14* (2006.01)
*A43B 7/14* (2006.01)
(Continued)

(52) U.S. Cl.
CPC ............ *A43B 7/146* (2013.01); *A43B 3/0005* (2013.01); *A43B 9/12* (2013.01); *A43B 13/203* (2013.01);
(Continued)

(58) Field of Classification Search
CPC ......... A43B 7/146; A43B 3/0005; A43B 9/12; A43B 13/203; A43B 23/029; A43B 7/1495; A61F 5/14
(Continued)

(56) References Cited

U.S. PATENT DOCUMENTS 3,888,242 A * 6/1975 Harris .................. A61H 9/0078 36/141
5,592,759 A * 1/1997 Cox ..................... A43B 1/0054 36/136

(Continued)

*Primary Examiner* — Timothy K Trieu
(74) *Attorney, Agent, or Firm* — Hamre, Schumann, Mueller & Larson, P.C.

(57) ABSTRACT

A massaging shoe and a method for manufacturing the same are provided. The massaging shoe comprises a shoe body formed by a shoe sole (10) and a shoe vamp (20) connected together, and further comprises a sock sleeve (50) detachably arranged in the shoe body, the sock sleeve (50) is provided with at least one massaging air bag (30), the shoe sole includes a shoe sole body (11) having a containing cavity and a shoe board (12) covering on the containing cavity, and the containing cavity is provided therein with an air pump (41) communicating with the massaging air bag (30) and electronic components (40) controlling the air pump (41). In the present invention, the massaging air bag (30) is arranged in the sock sleeve (50), the sock sleeve (50) is arranged in the shoe body, and the massaging air bag (30) is communicated with the air pump (41) to form a massaging shoe. Since the sock sleeve (50) is detachable, it is convenient to detach and clean the sock sleeve (50) after use; if the massaging air bag (30) is damaged, the massaging air bag (30) and the sock sleeve (50) can be replaced directly, and the shoe body does not need to be disassembled, such that it is convenient to repair; moreover, this massaging shoe is simple in manufacture, has a high machining efficiency, and has low cost.

12 Claims, 5 Drawing Sheets

(51) Int. Cl.

| | |
|---|---|
| ***A43B 3/00*** | (2006.01) |
| ***A43B 9/12*** | (2006.01) |
| ***A43B 13/20*** | (2006.01) |
| ***A43B 23/02*** | (2006.01) |
| ***A43B 23/07*** | (2006.01) |
| ***A61H 7/00*** | (2006.01) |
| ***A61H 9/00*** | (2006.01) |

(52) U.S. Cl.
CPC ............ *A43B 23/029* (2013.01); *A43B 23/07* (2013.01); *A61H 7/007* (2013.01); *A61H 9/0078* (2013.01); *A61H 2201/0103* (2013.01); *A61H 2201/0157* (2013.01); *A61H 2201/1207* (2013.01); *A61H 2201/1238* (2013.01); *A61H 2201/1409* (2013.01); *A61H 2201/164* (2013.01); *A61H 2201/165* (2013.01); *A61H 2205/12* (2013.01); *A61H 2205/125* (2013.01)

(58) Field of Classification Search
USPC ........................................................ 36/55, 141
See application file for complete search history.

(56) References Cited

U.S. PATENT DOCUMENTS

| | | | | |
|---|---|---|---|---|
| 5,868,690 | A * | 2/1999 | Eischen, Sr. ......... | A61H 9/0078 128/DIG. 20 |
| 6,725,573 | B2 * | 4/2004 | Doyle .................. | A43B 13/203 36/29 |
| 7,614,168 | B1 * | 11/2009 | Zummer ............ | A61H 15/0078 36/141 |
| 2011/0131839 | A1 * | 6/2011 | Ballin .................. | A43B 13/186 36/141 |
| 2012/0047766 | A1 * | 3/2012 | Moore ................... | A43B 3/242 36/1.5 |
| 2015/0305436 | A1 * | 10/2015 | Doyle .................. | A43B 13/203 36/43 |

* cited by examiner

MASSAGING SHOE AND METHOD FOR MANUFACTURING THE SAME

FIELD OF THE INVENTION

The present invention relates to the technical field of massagers, and more particularly relates to a massaging shoe and a method for manufacturing the same.

BACKGROUND OF THE INVENTION

There are various massaging shoes on the market. Most massaging shoes are made by assembling many independent components. Thus, the process is complicated, the machining efficiency is low, and the producing cost is high; furthermore, these massaging shoes are difficult to be cleaned and repaired.

SUMMARY OF THE INVENTION

A purpose of the present invention is to provide a massaging shoe and a method for manufacturing the same, which aim at solving the problem in the prior art that a process of manufacturing massaging shoes is complicated, a machining efficiency is low, and it is difficult to clean and repair the manufactured massaging shoes.

In order to solve the aforementioned technical problems, the present invention provides the following technical solution:

A massaging shoe is provided, the massaging shoe comprises a shoe body formed by a shoe sole and a shoe vamp connected together, and further comprises a sock sleeve detachably arranged in the shoe body; the sock sleeve is provided with at least one massaging air bag, the shoe sole includes a shoe sole body having a containing cavity and a shoe board covering on the containing cavity, and the containing cavity is provided therein with an air pump communicating with the massaging air bag and electronic components controlling the air pump.

Alternatively, the sock sleeve includes an outer sleeve and an inner sleeve arranged in the outer sleeve and detachably connected with the outer sleeve, and the massaging air bag is arranged between the outer sleeve and the inner sleeve.

Alternatively, the massaging air bag includes a first massaging air bag unrolled between the inner sleeve and the outer sleeve and configured to massage a foot sole correspondingly, the first massaging air bag includes a plurality of air bag cells, and under control of the electronic components, the plurality of air bag cells are inflated and deflated synchronously or are inflated and deflated in sequence.

Alternatively, the massaging air bag further includes a second massaging air bag, and the second massaging air bag is arranged to correspond to a front inner wall of the shoe vamp.

Alternatively, the massaging air bag further includes a third massaging air bag, and the third massaging air bag is arranged on a rear inner wall of the shoe vamp and corresponds to a heel.

Alternatively, an inside of the third massaging air bag is provided with at least one massaging head.

Alternatively, the inside of the third massaging air bag is provided with two massaging heads, and the two massaging heads are arranged abreast and tilt inwardly.

Alternatively, opened portions of the outer sleeve and the inner sleeve are fixedly connected together by means of a zipper, a button, or a velcro.

Alternatively, the shoe board defines an assembly opening, the massaging air bag is provided with a nozzle, the nozzle runs through the assembly opening, extends into the containing cavity, and communicates with the air pump, and the nozzle is secured at the assembly opening by a latch.

The present invention further provides a method for manufacturing a massaging shoe, which comprises the following steps:

a preparation step:

preparing a shoe sole, and arranging an air pump and electronic components controlling the air pump in the shoe sole;

preparing a shoe vamp; and preparing a sock sleeve, and arranging at least one massaging air bag in the sock sleeve;

an assembling step:

securing the shoe vamp onto the shoe sole to form a shoe body, placing the sock sleeve with the massaging air bag mounted thereon into the shoe body, and communicating the massaging air bag with the air pump.

In particular, when preparing the sock sleeve, an outer sleeve and an inner sleeve that is capable of being sleeved in the outer sleeve are prepared; the massaging air bag is arranged between the outer sleeve and the inner sleeve, and the outer sleeve is detachably connected with the inner sleeve at an opening thereof.

In particular, the shoe sole includes a shoe sole body having a containing cavity, a shoe board covering on the containing cavity, and a bottom plate arranged at a bottom of the shoe sole body, and the shoe board defines an assembly opening; when preparing the shoe sole, the air pump and the electronic components are placed in the containing cavity, and the shoe board is covered on the containing cavity; in the assembling step, a nozzle of the massaging air bag is driven to run through the assembling opening, extends into the containing cavity, and communicates with the air pump; from a bottom of the containing cavity, the nozzle is secured at the assembly opening by a latch; and finally the bottom board is mounted.

In particular, the massaging air bag includes a first massaging air bag; when arranging the massaging air bag, the first massaging air bag is unrolled between the inner sleeve and the outer sleeve; the first massaging air bag includes a plurality of air bag cells, and under control of the electronic components, the plurality of air bag cells are inflated and deflated synchronously or are inflated and deflated in sequence.

In particular, the massaging air bag further includes a second massaging air bag, when arranging the massaging air bag, the second massaging air bag is arranged along a front inner wall of the shoe vamp and corresponds to an instep.

In particular, the massaging air bag further includes a third massaging air bag, when arranging the massaging air bag, the third massaging air bag is arranged on a rear inner wall of the shoe vamp and corresponds to a heel.

In the present invention, the massaging air bag is arranged in the sock sleeve, the sock sleeve is arranged in the shoe body, and the massaging air bag is communicated with the air pump to form a massaging shoe. Since the sock sleeve is detachable, it is convenient to detach and clean the sock sleeve after use; if the massaging air bag is damaged, the massaging air bag and the sock sleeve can be replaced directly, and the shoe body does not need to be disassembled, such that it is convenient to repair; moreover, this massaging shoe is simple in manufacture, has a high machining efficiency, and has low cost.

EXPLANATION FOR THE LABEL NUMBERS IN THE DRAWINGS

Figure 1:
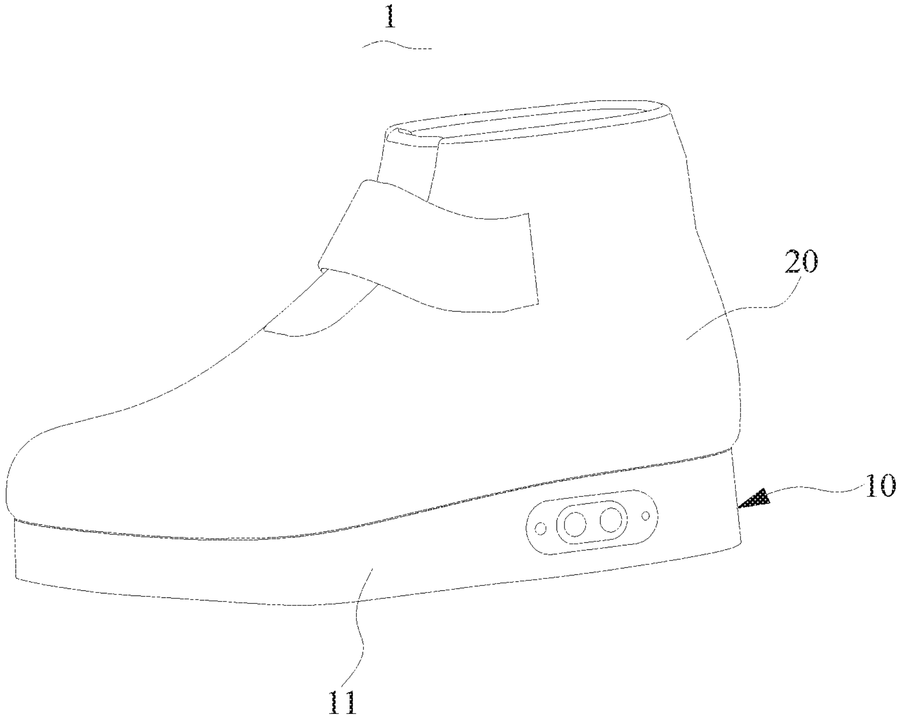
FIG. 1 is a structural schematic view of a massaging shoe provided by an embodiment of the present invention.

10—shoe sole; 11—shoe sole body; 111—switch button; 12—shoe board; 20—shoe vamp; 30—massaging air bag; 31—first massaging bag; 32—second massaging bag; 121—assembly opening; 33—third massaging bag; 331—massaging head; 40—electronic component; 41—air pump; 50—sock sleeve; 31—outer sleeve; 52—inner sleeve; 34—nozzle; 60—latch.

DETAILED DESCRIPTION OF THE PREFERRED EMBODIMENT

In order to make the purposes, technical solutions, and advantages of the present invention be clearer, the present invention will be further described in detail hereinafter with reference to accompany drawings and embodiments. It should be understood that the specific embodiments described here are only intended to illustrate the present invention, but not to limit the present invention.

It needs to be explained that when one element is referred to as "fixed" or "arranged" on another element, it may be directly located on the another element, or an intermediate element may exist simultaneously. When one element is referred to as "connected" with another element, it may be directly connected with the another element, or an intermediate element may exist simultaneously.

It needs to be further explained that the position terms in embodiments of the present invention, such as left, right, upper, lower, and so on, are only mutually relative concepts or take a normally used status of a product as reference, but should not be considered as having any limitation.

Referring to FIGS. 1-5, a massaging shoe provided by an embodiment of the present invention comprises a shoe body 1 formed by a shoe sole 10 and a shoe vamp 20 connected together, and further comprises a sock sleeve 50 detachably arranged in the shoe body 1; the sock sleeve 50 is provided therein with at least one massaging air bag 30, the shoe sole 10 includes a shoe sole body 11 having a containing cavity (not shown in the drawings) and a shoe board 12 covering on the containing cavity, and the containing cavity is provided therein with an air pump 41 communicating with the massaging air bag 30 and electronic components 40 controlling the air pump 41.

In this embodiment, the massaging air bag 30 is arranged in the sock sleeve 50, the sock sleeve 50 is arranged in the shoe body 1, and the massaging air bag 30 is communicated with the air pump 41 to form a massaging shoe. Since the sock sleeve 50 is detachable, it is convenient to detach and clean the sock sleeve 50 after use; if the massaging air bag 30 is damaged, the massaging air bag 30 and the sock sleeve 50 can be replaced directly, and the shoe body 1 does not need to be disassembled, such that it is convenient to repair.

Figure 2:
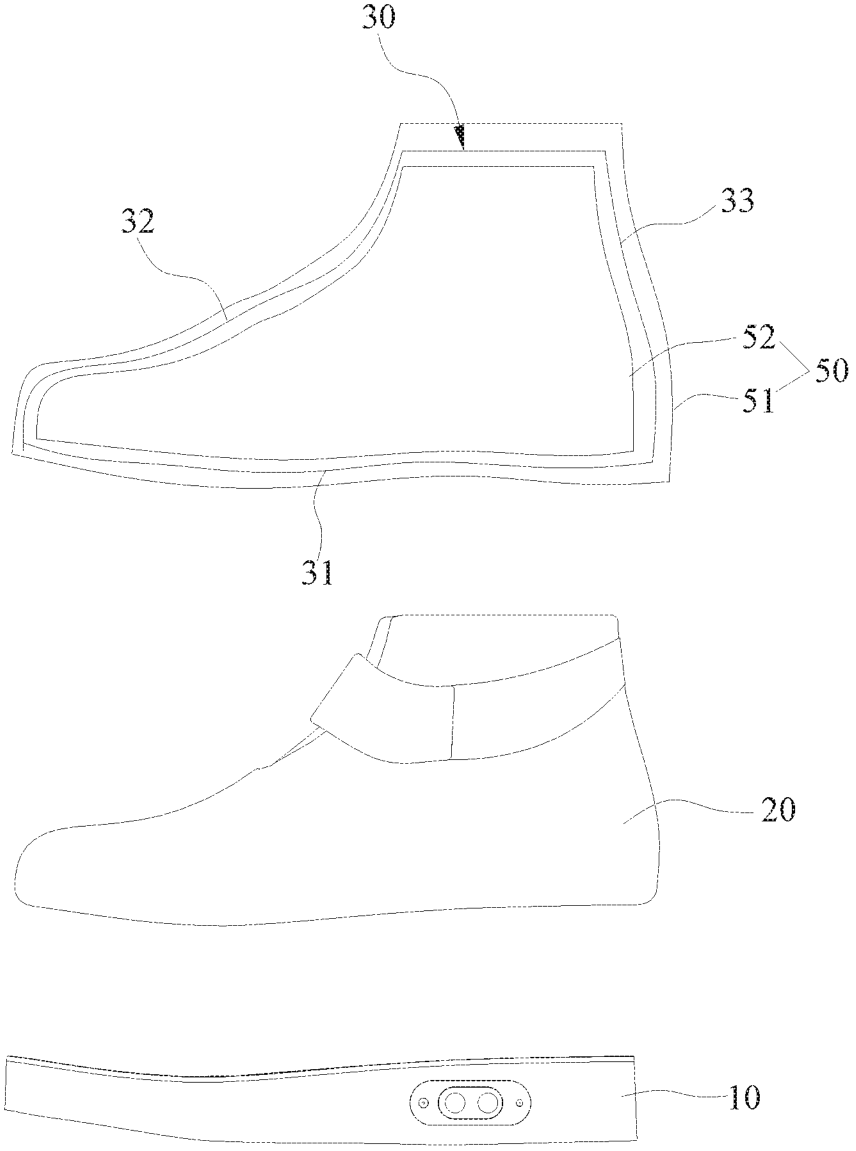
FIG. 2 is a disassembled schematic view of a massaging shoe provided by an embodiment of the present invention.

As shown in FIG. 2, the sock sleeve 50 is made of cloth, and includes an outer sleeve 51 made of cloth and an inner sleeve 52 made of cloth; the inner sleeve 52 is arranged in the outer sleeve 51, and the massaging air bag 30 is arranged between the outer sleeve 51 and the inner sleeve 52. The outer sleeve 51 is detachably connected with the inner sleeve 52. In particular, opened portions of the outer sleeve 51 and the inner sleeve 52 are fixedly connected together by means of a zipper, a button, or a velcro. In assembly, the massaging air bag 30 is arranged between the outer sleeve 51 and the inner sleeve 52 firstly, the inner sleeve 52 is then fixedly connected with the outer sleeve 51 by means of a zipper, a button, or a velcro, and finally the sock sleeve 50 is placed into the shoe body 1.

An upper surface of the shoe board 12 is a curved surface, which matches with a foot sole. In this way, the shoe board 12 can fit a foot sole better when massaging, such that the massaging effect is better. There are a plurality of massaging air bags 30, which include a first massaging air bag 31 unrolled between the inner sleeve 52 and the outer sleeve 51; the first massaging air bag 31 is communicated with the air pump 41 via a gas conduit (not shown in the drawings), and control for the air pump 41 is realized by the electronic components 40, such as an electromagnetic valve. The first massaging air bag 31 has a plurality of air bag cells (not shown in the drawings); under control of the electronic components 40, the plurality of air bag cells are inflated and deflated synchronously or are inflated and deflated in sequence. Compared with massaging using convex points, massaging a foot sole using the air bag cells is more comfortable and suitable for massaging for a long time. A user can select massaging a whole foot sole synchronously or massaging a part of the foot sole according to his/her requirement, such that the massaging effect is better. Moreover, the plurality of air bag cells massage different acupoints on the foot sole, and thus they can act on different organs. Frequent massaging can facilitate continuous circulation of blood, and in particular, massaging for a person with a sub-healthy body can accelerate metabolism of his/her body, such that some illnesses are eliminated from the body.

In this embodiment, the massaging air bag 30 further includes a second massaging air bag 32, the second massaging air bag 32 is arranged along a front inner wall of the shoe vamp 20 and corresponds to an instep. The second massaging air bag 32 is arranged here and configured to massage an instep.

The massaging air bag 30 further includes a third massaging air bag 33, the third massaging air bag 33 is arranged on a rear inner wall of the shoe vamp 20 and corresponds to a heel. By the third massaging air bag 33, an ankle can be massaged; particularly, after walking for a long time or strenuous exercise, an ankle can be relaxed effectively.

Figure 3:
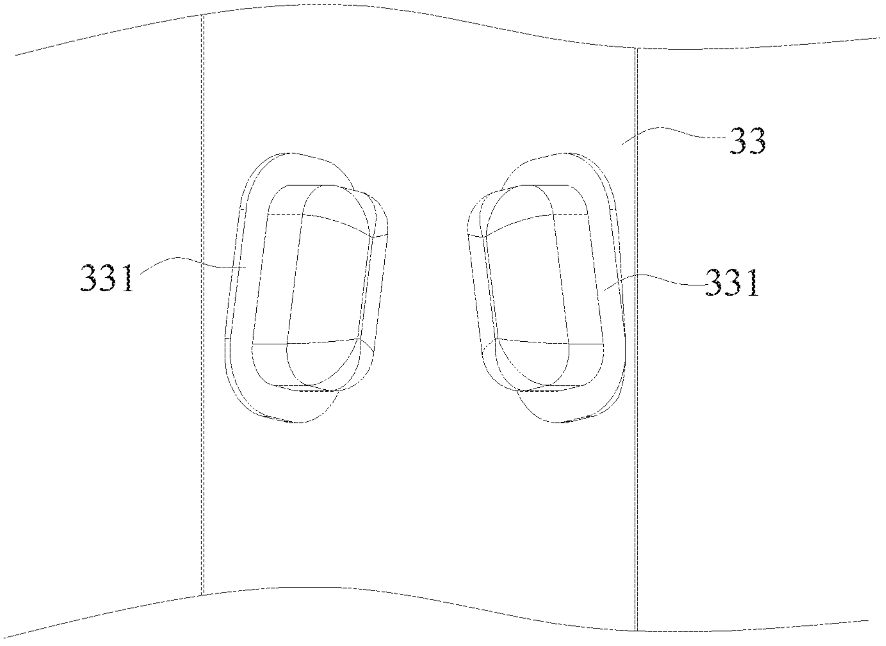
FIG. 3 is a structural schematic view of massaging heads arranged at a third massaging air bag of an embodiment of the present invention.
Figure 4:
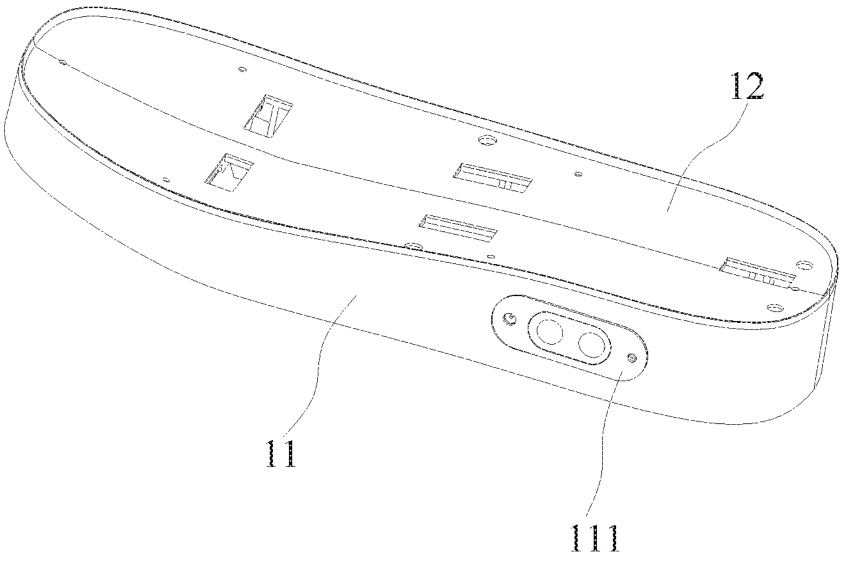
FIG. 4 is a structural schematic view of a shoe sole of an embodiment of the present invention.
Figure 5:
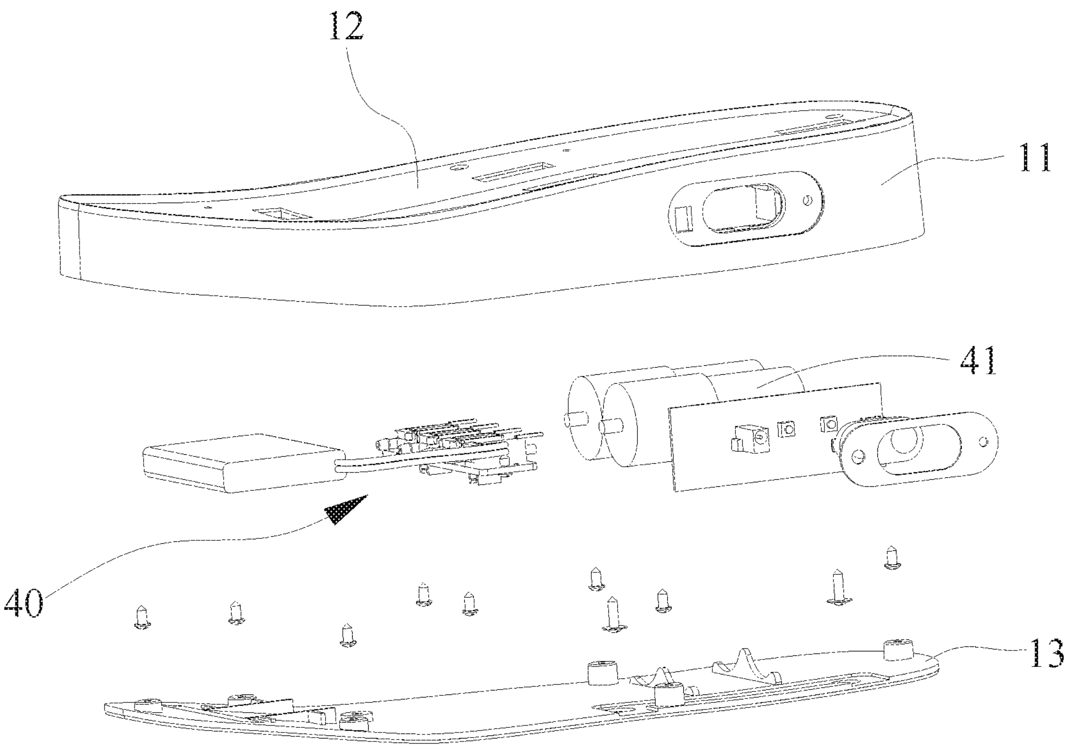
FIG. 5 is a disassembled schematic view of a shoe sole of an embodiment of the present invention.

Furthermore, in order to improve the massaging effect, referring to FIG. 3, the inside of the third massaging air bag 33 is provided with at least one massaging head 331. In this embodiment, there are two massaging heads 331, and the two massaging heads 331 are arranged abreast and tilt inwardly. In this way, the two massaging heads 331 can simulate kneading by a man's hand to massage, and thus the massaging effect is better.

In this embodiment, a side wall of the shoe sole body 11 is provided with a switch button 111, and the switch button 111 is electrically connected with the inner electronic components 50 to control the massaging shoe to be turned on and off.

Figure 6:
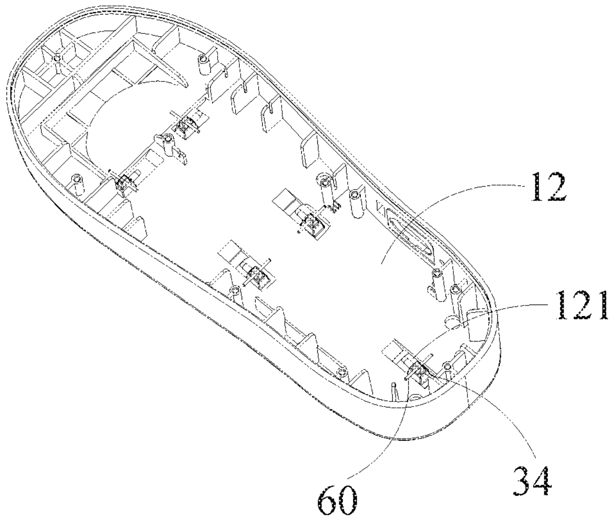
FIG. 6 is a rear schematic view of a shoe sole body of an embodiment of the present invention, wherein a bottom board is removed.

Referring to FIG. 6, the shoe board 12 is provided with an assembly opening 121, and the massaging air bag 30 is provided with a nozzle 34; when the massaging air bag 30 is positioned, the nozzle 34 thereof runs through the sock sleeve 50, extends into the containing cavity through the assembly opening 121, and communicates with the air pump 41; the nozzle 34 is further secured at the assembly opening 121 by a latch 60.

Figure 7:
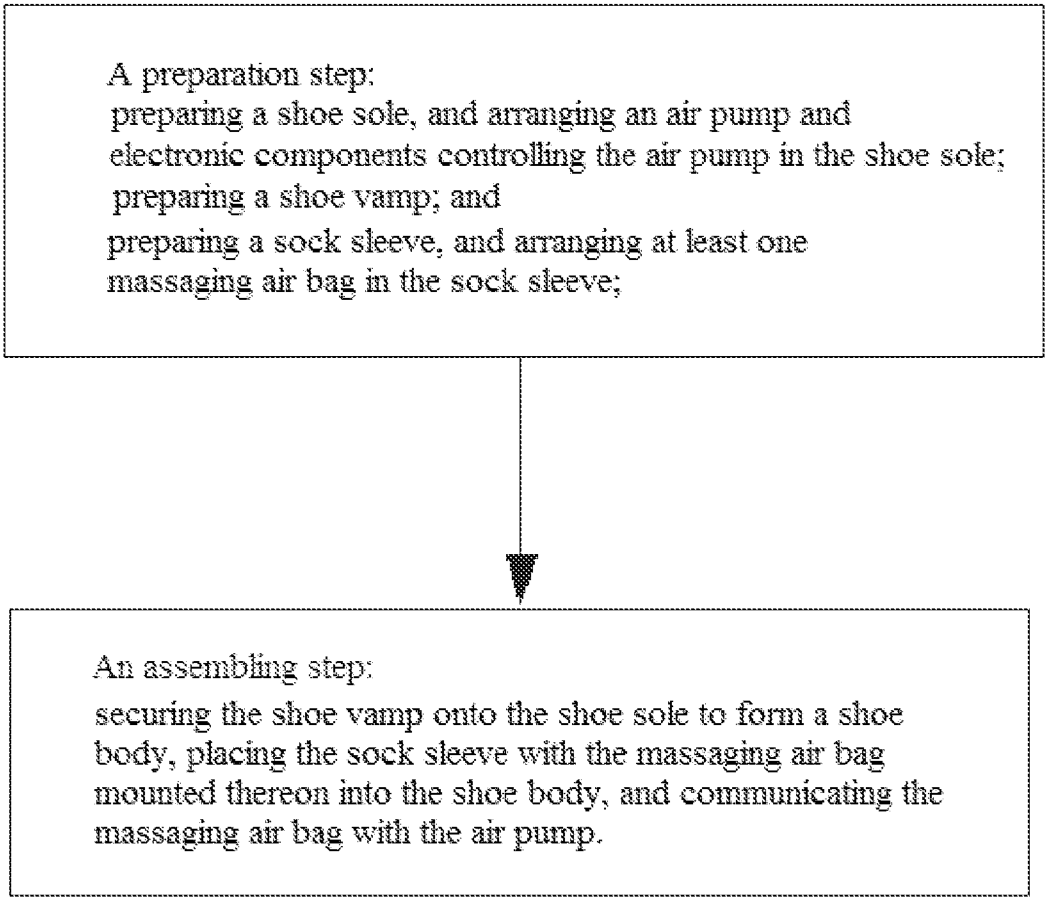
FIG. 7 is a flow chart of a method for manufacturing a massaging shoe provided by an embodiment of the present invention.

Referring to FIG. 7, the present invention further provides a method for manufacturing a massaging shoe, which comprises the following steps:

a preparation step:

preparing a shoe sole 10, and arranging an air pump 41 and electronic components 40 controlling the air pump 41 in the shoe sole 10; it needs to be explained that the shoe sole 10 is provided therein with a containing cavity, and the air pump 41 and the electronic components 40 are arranged in the containing cavity.

preparing a shoe vamp 20; wherein the shoe vamp 20 can have various structures, for example, it can be fabricated as a shoe vamp of a sport shoe, and can also be fabricated as a shoe vamp of a boot, or the like.

preparing a sock sleeve 50, and arranging at least one massaging air bag 30 in the sock sleeve 50; specifically, adopting cloth to fabricate an outer sleeve 51 and an inner sleeve 52, putting the inner sleeve 52 into the outer sleeve 51, arranging the massaging air bag 30 between the outer sleeve 51 and the inner sleeve 52, and detachably connecting opened portions of the outer sleeve 51 and the inner sleeve 52 together. In particular, the opened portions of the outer sleeve 51 and the inner sleeve 52 are fixedly connected together by means of a zipper, a button, or a velcro. In assembly, the massaging air bag 30 is arranged between the outer sleeve 51 and the inner sleeve 52 firstly, the inner sleeve 52 is then fixedly connected with the outer sleeve 51 by means of a zipper, a button, or a velcro, and finally the sock sleeve 50 is placed into the shoe body 1.

an assembling step: securing the shoe vamp 20 onto the shoe sole 10 to form a shoe body 1, wherein the fixing between the shoe vamp 20 and the shoe sole 10 is performed by a conventional method, that is, fixedly connecting by hot melt and adhesive.

finally, placing the sock sleeve 50 with the massaging air bag 30 mounted thereon into the shoe body 1, and communicating the massaging air bag 30 with the air pump 41, thereby forming the massaging shoe.

It needs to be explained that in the preparing step, the aforesaid shoe sole, shoe vamp, and sock sleeve can be directly fabricated, and can also be obtained by directly purchasing. Meanwhile, in the assembling step, the methods for fabricating the shoe vamp and the shoe sole can also adopt conventional methods. Therefore, in the method for manufacturing massaging shoes of the embodiment of the present invention, procedures are less, the assembly is simple, the product efficient is high, the cost is low, complicated machining apparatuses do not need to be provided additionally, and the manufactured massaging shoes have simple and compact structures and feel comfortable.

When preparing the shoe sole 10, the shoe sole 10 includes a shoe sole body 11 having a containing cavity, a shoe board 12 covering on the containing cavity, and a bottom plate 13 arranged at a bottom of the shoe sole body 11, and the shoe board 12 defines an assembly opening 121; when preparing the shoe sole 10, the air pump 41 and the electronic components 40 are placed in the containing cavity, and the shoe board 12 is covered on the containing cavity; the massaging air bag 30 is provided with a nozzle 34, in the assembling step, the nozzle 34 of the massaging air bag 30 is driven to run through the sock sleeve 50, extends into the containing cavity through the assembling opening 121, and communicates with the air pump 41; from a bottom of the containing cavity, the nozzle 34 is secured at the assembly opening 121 by a latch 60; and finally the bottom board 13 is mounted.

When preparing the massaging air bag 30, the massaging air bag 30 includes a first massaging air bag 31, the first massaging air bag 31 includes a plurality of air bag cells, and under control of the electronic components 40, the plurality of air bag cells are inflated and deflated synchronously or are inflated and deflated in sequence.

When preparing the massaging air bag 30, the massaging air bag 30 further includes a second massaging air bag 32 and a third massaging air bag 33.

Wherein, the first massaging air bag 31 is configured to massage a foot sole, a second massaging air bag 32 is configured to massage an instep, a third massaging air bag 33 is configured to massage an ankle; therefore, in assembly, the first massaging air bag 31 is unrolled between the inner sleeve 52 and the outer sleeve 51, the second massaging air bag 32 is arranged along a front inner wall of the shoe vamp 20 and corresponds to an instep, and the third massaging air bag 33 is arranged on a rear inner wall of the shoe vamp 20 and corresponds to a heel.

The above contents are only preferred embodiments of the present invention, and are not intended to limit the present invention. Any modification, equivalent replacement or improvement made within the spirit and principle of the present invention should be included in the protection scope of the present invention.

What is claimed is:

1. A massaging shoe comprising a shoe body formed by a shoe sole and a shoe vamp connected together, wherein the massaging shoe further comprises a sock sleeve detachably arranged in the shoe body, the sock sleeve is provided with at least one massaging air bag, the shoe sole includes a shoe sole body having a containing cavity and a shoe board covering on the containing cavity, the containing cavity is provided therein with an air pump communicating with the at least one massaging air bag and electronic components controlling the air pump, the sock sleeve includes an outer sleeve and an inner sleeve arranged in the outer sleeve and detachably connected with the outer sleeve, and the at least one massaging air bag is arranged between the outer sleeve and the inner sleeve, and the at least one massaging air bag includes a first massaging air bag unrolled between the inner sleeve and the outer sleeve and configured to massage a foot sole correspondingly.

2. The massaging shoe according to claim 1, wherein the at least one massaging air bag includes a second massaging air bag, and the second massaging air bag is arranged to correspond to a front inner wall of the shoe vamp.

3. The massaging shoe according to claim 1, wherein the at least one massaging air bag includes a third massaging air bag, and the third massaging air bag is arranged on a rear inner wall of the shoe vamp and corresponds to a heel of the massaging shoe.

4. The massaging shoe according to claim 3, wherein an inside of the third massaging air bag is provided with at least one massaging head.

5. The massaging shoe according to claim 1, wherein opened portions of the outer sleeve and the inner sleeve are fixedly connected together by means of a zipper, or a button.

6. The massaging shoe according to claim 1, wherein the shoe board defines an assembly opening, the massaging air bag is provided with a nozzle, the nozzle runs through the assembly opening, extends into the containing cavity, and communicates with the air pump, and the nozzle is secured at the assembly opening by a latch.

7. A massaging shoe comprising a shoe body formed by a shoe sole and a shoe vamp connected together, wherein the massaging shoe further comprises a sock sleeve detachably arranged in the shoe body, the sock sleeve including at least one massaging air bag, the shoe sole includes a shoe sole body having a containing cavity and a shoe board covering on the containing cavity, and the containing cavity is provided therein with an air pump communicating with the massaging air bag and electronic components controlling the air pump;

the at least one massaging air bag includes a third massaging air bag, and the third massaging air bag is arranged on a rear inner wall of the shoe vamp and corresponds to a heel of the massaging shoe;

an inside of the third massaging air bag is provided with two massaging heads, and the two massaging heads are arranged abreast and tilt inwardly towards each other.

8. The massaging shoe according to claim 7, wherein the sock sleeve includes an outer sleeve and an inner sleeve arranged in the outer sleeve and detachably connected with the outer sleeve, and the massaging air bag is arranged between the outer sleeve and the inner sleeve.

9. The massaging shoe according to claim 8, wherein the at least one massaging air bag includes a first massaging air bag unrolled between the inner sleeve and the outer sleeve and configured to massage a foot sole correspondingly.

10. The massaging shoe according to claim 7, wherein the at least one massaging air bag includes a second massaging air bag, and the second massaging air bag is arranged to correspond to a front inner wall of the shoe vamp.

11. The massaging shoe according to claim 8, wherein opened portions of the outer sleeve and the inner sleeve are fixedly connected together by means of a zipper or a button.

12. The massaging shoe according to claim 7, wherein the shoe board defines an assembly opening, the massaging air bag is provided with a nozzle, the nozzle runs through the assembly opening, extends into the containing cavity, and communicates with the air pump, and the nozzle is secured at the assembly opening by a latch.

* * * * *